(12) United States Patent
Baek et al.

(10) Patent No.: US 6,512,124 B1
(45) Date of Patent: Jan. 28, 2003

(54) BISPHENOL ARYL FLUORIDE AB2 MONOMER AND THE HYPERBRANCHED POLYMER THEREFROM

(75) Inventors: Jong-Beom Baek, Beavercreek, OH (US); Loon-Seng Tan, Centerville, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 10/083,968

(22) Filed: Feb. 27, 2002

(51) Int. Cl.[7] ............................................. C07D 209/48
(52) U.S. Cl. ...................................................... 548/476
(58) Field of Search ......................................... 548/476

(56) References Cited

PUBLICATIONS

Baek et al, *Chemical Abstracts*, vol. 137, No. 94104, 2002.*

* cited by examiner

*Primary Examiner*—Robert W. Ramsuer

(74) *Attorney, Agent, or Firm*—Charles Bricker; Thomas L. Kundert

(57) ABSTRACT

A self-polymerizable $AB_2$ monomer of the formula

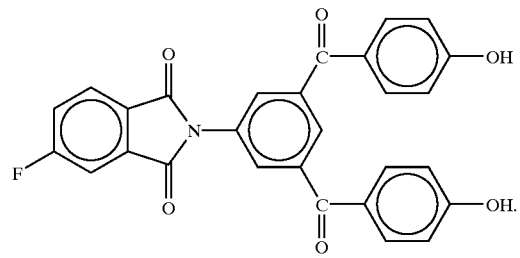

The resulting $AB_2$ monomer can be polymerized to afford high molecular, low viscosity hyperbranched ether-ketone-imide polymer having repeating units with hydroxyl end-groups.

1 Claim, No Drawings

BISPHENOL ARYL FLUORIDE AB2 MONOMER AND THE HYPERBRANCHED POLYMER THEREFROM

RIGHTS OF THE GOVERNMENT

The invention described herein may be manufactured and used by or for the Government of the United States for all governmental purposes without the payment of any royalty.

BACKGROUND OF THE INVENTION

The present invention relates to a novel $AB_2$ monomer, which can be polymerized to form hyperbranched polyimides.

Aromatic polyimides (PIs) are well known, high-performance materials with widespread applications in the aerospace and electronics industries due to their excellent thermomechanical and dielectric properties. Recently, it was demonstrated that they are useful as optical materials based on their optical anisotropy when cast in directions parallel (in-plane) and perpendicular (out-of-plane) to the film surface. However, when fully imidized, most aromatic PI's have limited solubility in common organic solvents, thus restricting the choice in processing options. Numerous research efforts have focused on organo-soluble PIs from the modification of the structure without substantially decreasing rigidity of their backbone. Solubility is desired in order to allow processing polymers with preformed imide units and to avoid the problems associated with handling poly (amic acid) (PAA) precursors. In addition, homogeneous, post-polymer reactions of soluble aromatic polyimides would allow better control in the introduction of desirable functional groups.

A viable alternative to attaining solubility in aromatic PIs is to change the traditional, linear geometry of the macromolecules to three-dimensional, highly branched (dendritic) architecture. As a subset of dendritic polymers, hyperbranched polymers have several important advantages such as better solubility compared to their linear counterparts, and easier synthesis than their analogous dendrimers, which involve tedious multi-step synthesis. Large quantity of hyperbranched polymers can be easily produced from $AB_x$ ($x \geq 2$) monomers. There are few reports on synthesis of hyperbranched PIs, and their utilization.

Accordingly, it is an object of the present invention to provide a self-polymerizable $AB_2$ monomer.

Other objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

SUMMARY OF THE INVENTION

In accordance with the present invention there is provided a self-polymerizable $AB_2$ monomer of the formula

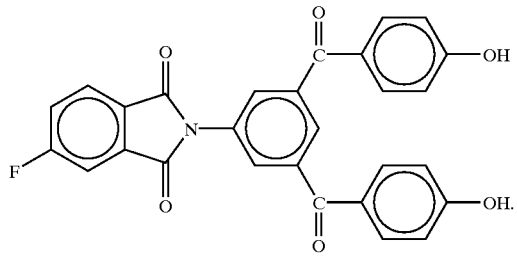

DETAILED DESCRIPTION OF THE INVENTION

Synthesis of the $AB_2$ monomer of this invention, N-{3,5-bis(4-hydroxybenzoyl)benzene}-4-fluoroisophthalimide, is shown by the following reaction sequence:

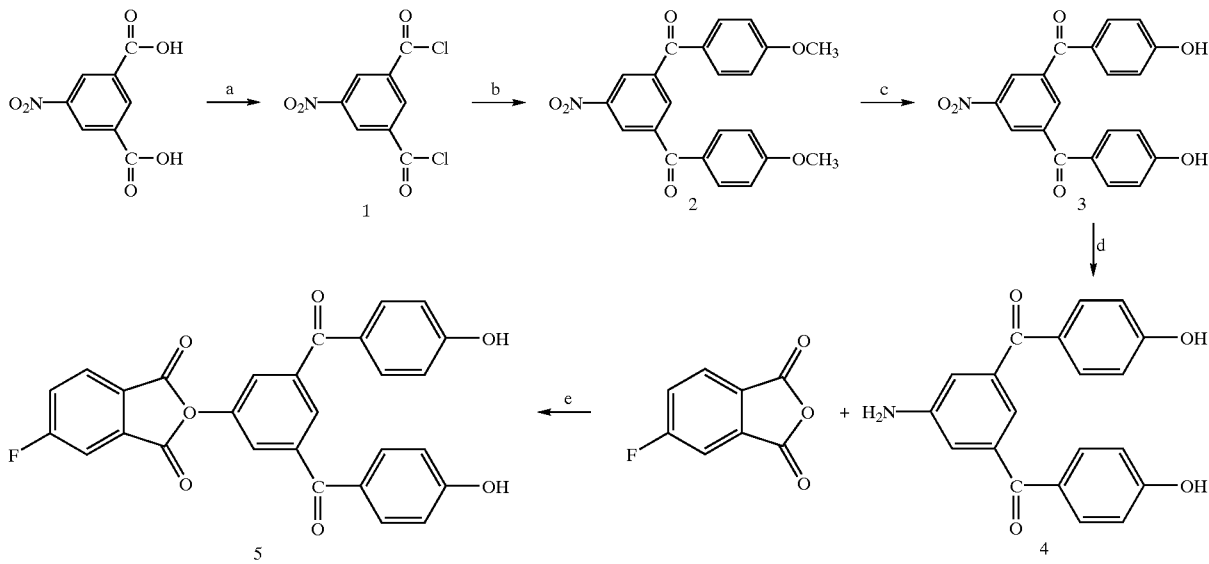

In this sequence, 5-nitroisophthalic acid is first treated with thionyl chloride (reaction a) to provide 5-nitroisophthaloyl dichloride (1). Friedel-Crafts reaction of 1 with anisole in the presence of aluminum chloride (reaction b) gives 3,5-bis(4-methoxybenzoyl)nitrobenzene (2), which is then demethylated with pyridine hydrochloride (reaction c) to provide 3,5-bis(4-hydroxybenzoyl) nitrobenzene (3). Compound 3 is then reduced (reaction d) to 3,5-bis(4-hydroxybenzoyl)aniline (4). Upon reacting with 4-fluoroisophthalic anhydride, with catalytic amount of isoquinoline, 4 is converted to the monomer 5, N-{3,5-bis (4-hydroxybenzoyl)benzene}-4-fluoroisophthalimide (reaction e).

The resulting $AB_2$ monomer can be polymerized in the presence of potassium carbonate under Dean-Stark conditions to afford high molecular, low viscosity hyperbranched ether-ketone-imide polymer having repeating units with hydroxyl endgroups:

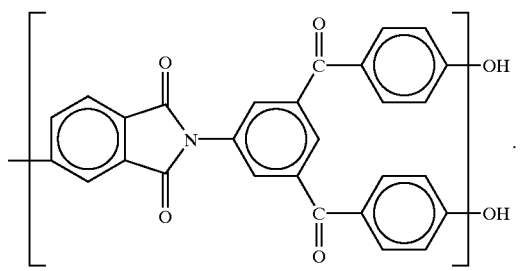

These endgroups can be readily converted to other useful and thermally reactive groups, such as, for example,

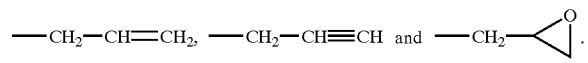

The polymers with reactive endgroups are key components of high-temperature matrix resins such as cyanate ester resins, phthalonitrile- and benzoxazine-based thermosets, and the like.

The following examples illustrate the invention:

Example 1

5-Nitroisophthaloyl Dichloride (1)

Into a 500 mL one-necked round bottom flask equipped with a magnetic stirrer and nitrogen inlet, 5-nitroisophthalic acid (25.0 g, 0.12 mol) was dissolved freshly distilled thionyl chloride (80 mL) containing DMF (3 drops). The mixture was stirred at room temperature for 2 h and gently heated under reflux for 6 h. Excess amount of thionyl chloride was distilled off and the mixture was then chilled in an ice-and-salt bath. Freshly distilled hexane was added into the light yellow residue with vigorous stirring. The resulting white needles are collected by suction filtration and dried under reduced pressure to give 29.1 g (99.1% yield) of white needles, m.p. 59–61.5° C. FT-IR (KBr, cm$^{-1}$): 1536, 1349 (Ar-NO$_2$), 1757 (carbonyl). Mass spectrum (m/e): 248 (M$^+$, 100% relative abundance). $^1$H-NMR (CDCl$_3$, δ in ppm): 8.96 (s, 2H, Ar), 9.12 (s, 1H, Ar). $^{13}$C-NMR (CDCl$_3$, δ in ppm): 127.89, 133.33, 136.12, 148.25, 165.35.

Example 2

3,5-Bis(4-Methoxylbenzoyl)nitrobenzene (2)

Into a 250 mL three-necked, round-bottomed flask equipped with a magnetic stirrer, nitrogen inlet, and dropping funnel, aluminum chloride (25.4 g, 0.19 mol) and anhydrous anisole (60 mL) were introduced. After the mixture was cooled down to 15° C. in an ice-water bath, a solution of 5-nitroisophthaloyl dichloride (15.0 g, 60 mmol) in anhydrous anisole was then added dropwise for 20 min. The mixture was allowed to warm to room temperature. After 8 h of stirring, the mixture was poured into 5% hydrochloric acid. The organic layer was diluted with methylene chloride, separated with the aid of a separatory funnel, and rotovapped to dryness. The resulting off-white solid residue was dissolved in hot ethanol and allowed to cool to room temperature to give 11.2 g (47.7% yield) of off-white solids, m.p. 181–182° C. Anal. Calcd. for $C_{22}H_{17}NO_6$: C, 67.52%; H, 4.38%; N, 3.58%; O, 24.53%. Found: C, 67.56%; H, 4.35%; N, 3.45%; O, 24.76%. FT-IR (KBr, cm$^{-1}$): 1538 (Ar-NO$_2$), 1262, 1325 (ether), 1598, 1655 (carbonyl). Mass spectrum (m/e): 391 (M$^+$, 100% relative abundance). $^1$H-NMR (DMSO-d$_6$; δ in ppm) 3.89 (s, 6H, OCH$_3$), 7.12–7.15 (d, 2H, Ar), 7.85–7.88 (d, 2H, Ar), 8.26 (t, 1 H, Ar), 8.61 (d, 2H, Ar). $^{13}$C-NMR (DMSO-d$_6$; δ in ppm) 55.61, 114.15, 126.27, 128.09, 132.47, 135.00, 139.18, 147.67, 163.57, 191.53.

Example 3

3,5-Bis(4-Hydroxybenzoyl)nitrobenzene (3)

Into a 250 mL three-necked, round-bottomed flask equipped with a magnetic stirrer, a condenser, and nitrogen inlet, 3,5-bis(4-methoxyphenylcarbonyl)nitrobenzene (6.2 g, 15.8 mmol) and freshly prepared pyridine hydrochloride (100 g) were placed. The mixture was heated under reflux until the solution became homogeneous. It took about 4 h. After cooled down 120° C., the mixture was poured into water. The resulting precipitate was collected and dried. The yellow solid was slurred in boiling toluene and collected by suction filtration to give 5.5 g (96% yield), m.p. 230–231.8° C. Anal. Calcd. for $C_{20}H_{13}NO_6$: C, 66.12%; H, 3.61%; N, 3.86%; O, 26.42%. Found: C, 66.07%; H, 3.64%; N, 3.67%; O, 17.01%. FT-IR (KBr, cm$^{-1}$): 1321, 1538 (A-NO$_2$), 1602, 1648 (carbonyl), 3420 (Ar-OH). Mass spectrum (m/e): 363 (M$^+$, 100% relative abundance). $^1$H-NMR (DMSO-d$_6$, δ in ppm): 6.93–6.96 (d, 4H, Ar), 7.76–7.79 (d, 4H, Ar), 8.23 (s 1H, Ar), 8.58 (s, 2H, Ar), 10.66 (s, 2H, OH). $^{13}$C-NMR (DMSO-d$_6$, δ in ppm) 115.48, 126.02, 126.65, 132.84, 134.83, 139.44, 147.61, 156.80, 162.70, 191.36.

Example 4

3,5-Bis(4-Hydroxybenzoyl)aminobenzene (4)

Into a 500 mL high pressure bottle, 5-nitroisophthalic acid (4.8 g, 13 mmol), palladium on activated carbon (10%, 0.5 g), and ethanol (100 mL) were charged. The bottle was placed on the hydrogenation vessel. Hydrogen was charged and discharged five times and agitated at 60–65 psi for 24 h. After the reaction mixture had been filtered through a cake of Celite 545 to remove catalyst, the solvent of the filtrate was removed on a rotary evaporator. The light yellow solid was recrystallized from deoxygenated 20% ethanol to give 4.4 g (>99% yield) of yellow powder, m.p. 249.5–250.5° C. Anal. Calcd. for $C_{20}H_{15}NO_4$: C, 72.06%; H, 4.54%; N, 4.20%; O, 19.20%. Found: C, 72.04%; H, 4.89%; N, 3.91%; O, 18.60%. FT-IR (KBr, cm$^{-1}$): 763 (Ar—NH$_2$), 1598 1634 (carbonyl), 3378 (Ar—NH$_2$). Mass spectrum (m/e): 333 (M$^{m+}$, 100% relative abundance). $^1$H-NMR (DMSO-d$_6$; δ in ppm): 5.71 (s, 2H, NH$_2$), 6.90–6.93 (d, 4H, Ar), 6.70 (s, 1H, Ar), 7.14 (s, 2H, Ar), 7.70–7.71 (d, 4H, Ar), 10.44 (s, 1H, OH). $^{13}$C-NMR (DMSO-d$_6$; δ in ppm): 115.10, 117.09, 117.55, 127.95, 132.35, 138.57, 148.91, 161.87, 194.21.

Example 5

N-{3,5-bis(4-Hydroxybenzoylbenzene)}-4-fluorophthalimide (5)

Into a 250 mL three-necked round-bottomed flask equipped with a magnetic stirrer and nitrogen inlet and outlet, 3,5-bis(4-hydroxyphenylcarbonyl)aminobenzene (4.3 g, 13 mmol) was completely dissolved in NMP (50 mL). 4-Fluorophthalic anhydride (2.1 g, 12 mmol) was then added. The mixture was then heated and when temperature was approaching 170–180° C., isoquinoline (5 drops) was added. The mixture was heated at 200° C. with stirring for 18 h. After cooled down to room temperature, the mixture was poured into 5% hydrochloric acid and the resulting precipitate was collected by suction filtration and dried under the reduced pressure. The off-white solid was dissolved in hot toluene and allowed to cool to room temperature to give 4.3 g (72% yield) of off-white solid, m.p. 274–276° C. Anal. Calcd. for $C_{28}H_{16}FNO_6$: C, 69.86%; H, 3.35%; N, 2.91%. Found: C, 69.90%; H, 3.90%; N, 2.66%. FT-IR (KBr, cm$^{-1}$): 1644, 1601 (imide), 1724 (carbonyl) 3413 (Ar-OH). Mass spectrum (m/e): 481 (M$^+$, 100% relative abundance). $^1$H-NMR (DMSO-d$_6$, δ in ppm): 6.93–6.96 (d, 4H, Ar), 7.71–7.75 (d, 1 H, Ar), 7.78–7.82 (d, 4H, Ar), 7.89–7.93 (dd, 1H, Ar), 7.96–7.97 (t, 1H, Ar), 8.05–8.07 (d, 1H, Ar), 8.09–8.10 (d, 2H, Ar), 10.58 (s, 2H, OH). $^{13}$C-NMR (DMSO-d6, δ in ppm) 111.44, 115.36, 121.38, 126.30, 127.11, 127.71, 128.95, 130.45, 132.70, 134.65, 138.43, 162.36, 163.97, 165.47, 165.73, 167.71, 192.45.

Example 6

Hyperbranched Polymer Derived from N, N'-Bis(3-Acetylphenyl)-4, 4'-(hexafluoroisopropylidene) diphthalimide Into a 100 mL three-necked, round-bottomed flask equipped with a magnetic stirrer, nitrogen inlet and outlet, and Dean-Stark trap with a condenser, N-[3,5-bis(4-hydroxybenzoyl)benzene]-4-fluorophthalimide (1.5 g, 3.1 mmol), potassium carbonate (1.0 g, 7.2 mmol), and a mixture of NMP (30 mL) and toluene solvent were placed. The reaction mixture was then heated and maintained at 140–150° C. for 4 h. During this time period, the water formed was removed by toluene azeotropic distillation via a Dean-Stark trap. After complete removal of toluene by an increased the flow of nitrogen, the orange solution was then heated at 160° C. for 3 h. The solution became brown in color and viscous. Some precipitate was observed 30min after reaction temperature had reached 160° C. After being allowed to cool down on its own, the mixture was poured into a beaker containing 5% hydrochloric acid (300 mL). The resulting precipitate was collected by suction filtration and air-dried. Off-white powder was dissolved in NMP again and passed through a cake of Celite 545 to remove any insoluble salts. The filtrate was poured in a beaker containing 5% hydrochloric acid (300 mL) and warmed up to around 60–70° C. for 2 h. The white powder was collected and dried under the reduced pressure over phosphorus pentoxide at 100° C. for 48h. The yield was essentially quantitative. [η]=0.13 dL/g. $T_g$=224° C. Anal. Calcd. for $C_{28}H_{15}NO_6$: C, 72.88%; H, 3.28%; N, 3.06%. Found: C, 68.55%; H, 3.93%; N, 3.01%. $^1$H-NMR (DMSO-d$_6$; δ in ppm) 6.89–8.39 (Ar-H) and 10.55–10.84 (Ar-OH) .Thermogravemetric analysis result indicates that this hyperbranched polymer lost 5% of its original weight about 400° C. in air and 416 ° C. in helium, respectively.

Having thus described exemplary embodiments of the present invention, it should be noted by those skilled in the art that the disclosures herein are exemplary only and that alternatives, adaptations and modifications may be made within the scope of the present invention.

We claim:

1. N-{3,5-bis(4-hydroxybenzoyl)benzene}-4-fluoroisophthalimide.

* * * * *

UNITED STATES PATENT AND TRADEMARK OFFICE
CERTIFICATE OF CORRECTION

PATENT NO.    : 6,512,124 B1
DATED         : January 28, 2003
INVENTOR(S)   : Jong-Beom Baek et al.

It is certified that error appears in the above-identified patent and that said Letters Patent is hereby corrected as shown below:

Column 1,
Lines 15, 22 and 34, "Pls" should read -- PIs --.
Between lines 50 and 62, product 5 should read --
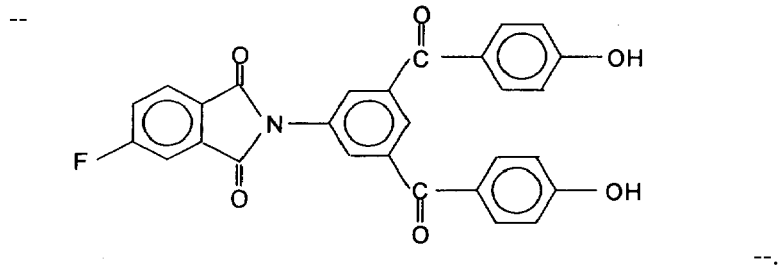
--.

Column 2,
Line 6, "Pls" should read -- PIs --.

Column 4,
Line 57, "$M^{m+}$" should read -- $M^+$ --.

Signed and Sealed this

Eighth Day of July, 2003

JAMES E. ROGAN
*Director of the United States Patent and Trademark Office*